(12) United States Patent
Gross et al.

(10) Patent No.: US 7,733,742 B2
(45) Date of Patent: Jun. 8, 2010

(54) METHOD AND INSTALLATION FOR ACOUSTO-OPTIC IMAGING

(75) Inventors: Michel Gross, Villepinte (FR); Francois Georges Gerard Ramaz, Le Kremlin-Bicetre (FR); Benoit Claude Forget, Paris (FR); Gerald Roosen, La Celle les Bordes (FR); Philippe Delaye, Paris (FR); Albert-Claude Boccara, Paris (FR)

(73) Assignees: Centre National de la Recherche Scientifique (CNRS), Paris Cedex (FR); Universite Pierre et Marie Curie (Paris VI), Paris (FR)

( * ) Notice: Subject to any disclaimer, the term of this patent is extended or adjusted under 35 U.S.C. 154(b) by 456 days.

(21) Appl. No.: 11/570,252

(22) PCT Filed: Jun. 10, 2005

(86) PCT No.: PCT/FR2005/001446

§ 371 (c)(1),
(2), (4) Date: Dec. 8, 2006

(87) PCT Pub. No.: WO2006/005836

PCT Pub. Date: Jan. 19, 2006

(65) Prior Publication Data

US 2008/0037367 A1    Feb. 14, 2008

(30) Foreign Application Priority Data

Jun. 17, 2004   (FR) ................. 04 06592

(51) Int. Cl.
*H04B 11/00* (2006.01)
(52) U.S. Cl. .................................................. 367/191
(58) Field of Classification Search ............ 367/81–191
See application file for complete search history.

(56) References Cited

U.S. PATENT DOCUMENTS

| | | | | |
|---|---|---|---|---|
| 3,474,402 | A * | 10/1969 | Bealor, Jr. et al. ............ | 367/155 |
| 6,175,411 | B1 * | 1/2001 | Telschow et al. ............ | 356/503 |
| 2001/0028460 | A1 * | 10/2001 | Maris et al. .................. | 356/432 |
| 2003/0043696 | A1 * | 3/2003 | Vakoc .......................... | 367/149 |
| 2006/0272419 | A1 * | 12/2006 | Maris et al. ................... | 73/606 |

* cited by examiner

*Primary Examiner*—Thomas H Tarcza
*Assistant Examiner*—Luke D Ratcliffe
(74) *Attorney, Agent, or Firm*—Miller, Matthias & Hull

(57) ABSTRACT

This invention concerns an acousto-optic imaging method comprising a step which consists in engraving in a dynamic holographic material a complex index array resulting from the interference of the acousto-optic component of the signal wave and a pump wave of frequency equal to the frequency of the acousto-optic component.

27 Claims, 2 Drawing Sheets

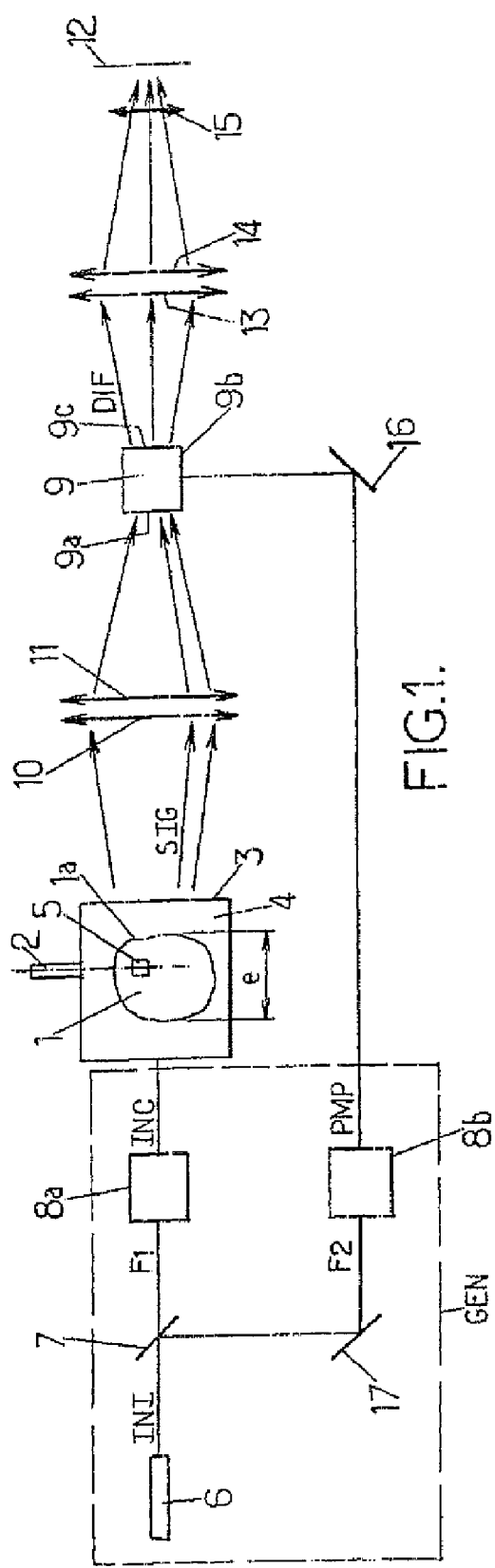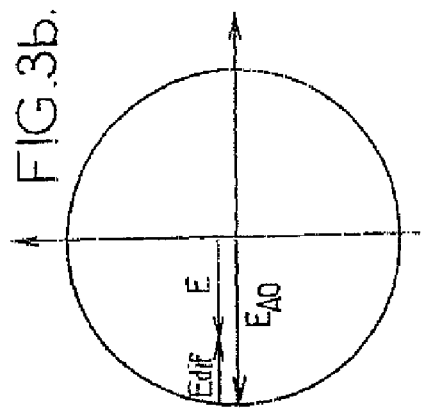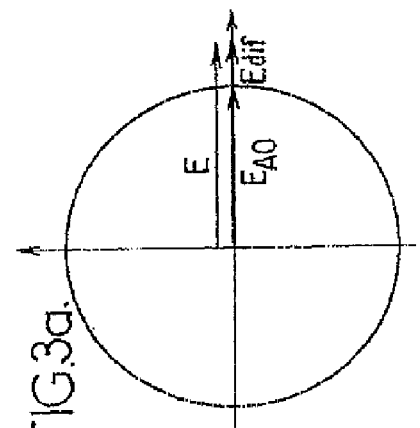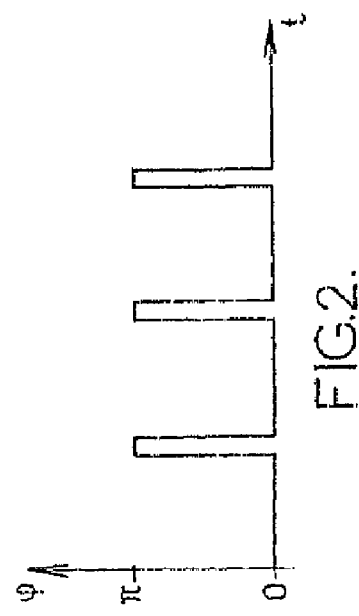

METHOD AND INSTALLATION FOR ACOUSTO-OPTIC IMAGING

CROSS-REFERENCE TO RELATED APPLICATION

This is the U S. National Phase of International Application No. PCT/FR2005/01446 filed 10 Jun. 2005, the entire disclosure of which is incorporated herein by reference

FIELD OF THE DISCLOSURE

The present invention relates to acousto-optic imaging methods and installations.

BACKGROUND OF THE DISCLOSURE

More particularly, the invention relates to an acousto-optic imaging method.

In this type of method, an object to be imaged is illuminated with a laser-type light source. Moreover, acoustic waves are propagated in the object by an ultrasound source. Information is obtained for an area of the object to be imaged by detecting a signal linked to the coupling properties between the light wave and the ultrasound wave which specifically makes the concerned area vibrate. In practice, when an ultrasound wave, of acoustic frequency $f_a$ passes through a scattering medium (such as, for example, a biological tissue, or other), it provokes a periodic shaking of the scatterers and a periodic modulation of the refraction index of the medium. If a laser wave, of incident frequency $f_I$, is scattered by the medium, the movement of the scatterers and the modulation of the index of the medium generate a signal wave comprising on the one hand a carrier component (at the frequency $f_I$) and on the other hand, an acousto-optic component scattered on one or other of the acoustic side-bands (of frequency $f_{AO}=f_a\pm f_I$). Acousto-optic imaging consists in determining the weight of this component at the frequency $f_{AO}$ according to the focal position of the acoustic wave in the diffusing medium.

Historically, detection was initially performed using a single-pixel detector. However, this technique offers poor sensibility.

In practice, the detection is achieved by measuring the interferences between two components of the signal wave: the carrier component, at the frequency $f_I$, and the acousto-optic component, at the frequency $f_{AO}$. Since these two frequencies differ from each other roughly by the value of the acoustic frequency $f_a$ of the ultrasound wave, the detection is heterodyne. Such a detection is effective only for a very small geometric expanse, such that most of the signal is lost.

Also, because of the presence of diffusers in the medium, the carrier and acousto-optic components of the signal wave are two random speckle fields, such that the relevant information is obtained only by spatially and/or temporally averaging the detected signal.

A major improvement was provided by the ESPCI (see in particular "Ultrasonic tagging of photon paths in scattering media: parallel speckle modulation", Levêque et al., published in *Optic Letters* 24: 181, 1999). In this device, the single-pixel detector is replaced by a multiple-pixel detector such as a CCD camera. There is, however, a problem in that such a camera is too slow to detect an interference signal between the carrier and acousto-optic components of the signal wave, which has a high frequency, of the order of that of the acoustic wave (a few MHz, typically). To detect a signal, the ESPCI no longer detects the interferences of the acousto-optic component with the carrier component, but with a reference component passing through the medium and obtained by amplitude modulation of the incident wave at a frequency close to that of the acousto-optic component (typically, to within a few Hz). There is thus obtained an interference between the reference component and the acousto-optic component which is slow enough to be detected for each pixel of the camera. To obtain the information relating to the vibrating area, the detected signal must be summed over all the pixels of the camera.

This technique is not, however, the best possible because, on the one hand, the measured signal includes a significant noise component due to the photons that are simply scattered having passed through an area of the object to be imaged that is not vibrating, and on the other hand, the reference component is relatively weak, because it passes through the scattering medium.

Furthermore, each of the signals carries a so-called "speckle decorrelation" noise. The light, scattered by the medium, is emitted in the form of a speckle wave, made up of grains. From one speckle grain to the next, the amplitude and the phase of the signal wave vary randomly. If, over time, the scattering medium is modified (such is in particular the case for living tissues), the scatterers change position. This modifies the position, the intensity and the phase of the speckle grains (the speckle is said to be decorrelated).

In acousto-optic imaging, the overall intensity of the acousto-optic component of the signal wave is to be measured. The latter is much weaker than that corresponding to the acoustically unmarked component (the carrier component or the reference component, depending on the used technique), which is also seen by the detector. If a continuous part associated with the acoustically unmarked component can easily be eliminated during the detection, the amplitude and phase variations of the signal wave, which are reflected by the decorrelation of the speckle, often lead to a false signal called "speckle decorrelation noise".

Living biological tissues, for which the acousto-optic imaging technique is required to be used, for example in screening for breast cancer, or other purposes, lead to a major speckle decorrelation noise. It is therefore preferable to be able to perform rapid measurements, for which the use of multiple-pixel detectors, which are rather slow is not well suited. There is therefore a lack of a method that can guarantee a good measurement sensitivity for biological tissues.

SUMMARY OF THE DISCLOSURE

To this end, according to the invention, there is provided an acousto-optic imaging method for an object comprising steps during which:

(a) the vibration of an area of the object is generated by applying an acoustic wave exhibiting a certain acoustic frequency to the object, (b) an incident light wave is applied to said object and a signal light wave is generated, comprising at least one acousto-optic component frequency-shifted by said acoustic wave, (c) a light pump wave is generated, coherent with said incident wave at a pump frequency equal to the frequency of said acousto-optic component, (d) a complex index grating is formed in a dynamic holographic material by applying said signal wave and said pump wave to said material, and (e) a digital parameter relating to the light intensity in this area is obtained from said complex index grating.

Thanks to these provisions, the noise caused by the unmarked component of the signal wave can be disregarded, because the index array is formed only for an interferogram of zero frequency between the acousto-optic component of the signal and the pump wave. Furthermore, it is possible to use a fast detector such as a photodiode when reading the dynamic holographic material.

In preferred embodiments of the invention, use can, if necessary, also be made of one and/or another of the following arrangements:

during the step (e),
(e1) a diffracted wave is generated by applying said pump wave to said complex index grating, and
(e2) the interference between said diffracted wave and said signal wave is detected using a photodetector;
a phase modulation is applied to a wave chosen from the acoustic wave, the pump wave, and the incident wave;
said phase modulation is applied to the acoustic wave;
an amplitude modulation is applied to a wave chosen from the acoustic wave, the pump wave, and the incident wave;
said amplitude modulation is applied to the acoustic wave;
the incident wave and the pump wave are generated by
generating an initial light wave using a laser,
splitting said initial wave into a first beam (F1) and a second beam,
shifting the frequency of said first beam by a first frequency shift to generate the incident wave,
shifting the frequency of said second beam by a second frequency shift to generate the pump wave, said second frequency shift being roughly equal to the sum of the first frequency shift and the acoustic frequency;
one of said first and second frequency shifts is zero;
during the step (d), said signal wave is applied to a first side of said dynamic holographic material and said pump wave is applied to a second side of said material, different from the first side;
during the step (d), said signal wave and said pump wave are applied to one and the same side of the dynamic holographic material;
said dynamic holographic material is a photo-refractive crystal adapted to operate in "energy transfer" mode;
said dynamic holographic material is a photo-refractive crystal adapted to operate in "anisotropic diffraction" mode;
digital information is also obtained relating to a second area of the object by applying the following steps:
the vibration of said second area is generated by applying an acoustic wave at an acoustic frequency to the object at said second area, and
the steps (b) to (e) are repeated for said second area.

According to another aspect, the invention relates to an acousto-optic imaging installation for an object comprising:

(A) a transducer designed to generate the vibration of an area of the object by applying an acoustic wave having an acoustic frequency to the object;
(B) a device for generating light waves designed to apply to said object an incident light wave and thus generating a signal light wave comprising at least one acousto-optic component frequency-shifted by said acoustic wave, and also designed to generate a light pump wave, coherent with said incident wave at a frequency similar to the frequency of said acousto-optic component;
(C) a dynamic holographic material adapted so that a complex index grating is formed by the application to said material of said signal wave and of said pump wave, and
(D) a detection device designed to obtain a digital parameter relating to the light intensity in this area from said complex index grating., According to alternative embodiments of the invention, use can also be made of one and/or another of the following arrangements:

the detection device comprises a detector designed to detect the interference between a diffracted wave generated by said pump wave passing through said complex index grating, and said signal wave;
said detector is a single-pixel photodiode,
the installation comprises:
a first optical device designed to apply the signal wave to a first side of the dynamic holographic material,
a second optical device designed to apply the pump wave to a second side of the dynamic holographic material, and
a third optical device designed to form on said detector an image of a third side of the dynamic holographic material opposite to said first side;
said first and second sides of dynamic holographic material are the same;
said second side of dynamic holographic material is orthogonal to said first side;
the generation device comprises:
a laser designed to emit an initial light wave,
a splitter device designed to generate from said initial wave a first beam and a second beam,
a first shift device designed to shift said first beam frequency-wise to generate said incident wave, and
a second shift device designed to shift said second beam frequency-wise to generate said pump wave,
said first and second shift devices being designed for said pump wave to exhibit a frequency roughly equal to the sum of the frequency of the incident wave and the frequency of the acoustic wave;
said first shift device comprises one, zero or two acousto-optic modulators, and said second shift device comprises, respectively, one, two, or zero acousto-optic modulators;
said dynamic holographic material is a photo-refractive crystal;
said dynamic holographic material is a population inversion material designed to be formed with a complex index grating in the form of a gain grating, said installation also comprising an energy source designed to maintain said population inversion in said material;
the installation also comprises a control device designed to cause said transducer to be displaced and/or the focal length of said transducer to be changed.

BRIEF DESCRIPTION OF THE DRAWINGS

Other characteristics and advantages of the invention will become apparent from the following description of one of its embodiments, given as a non-limiting example, in light of the appended drawings.

In the drawings:

FIG. 1 is a diagrammatic view of an acousto-optic imaging installation according to the invention, FIG. 2 is a time diagram representing a phase modulation of the acoustic wave, FIGS. 3a and 3b are a phase diagram representing the amplitudes of the various components in a photo-refractive crystal respectively on writing and on reading the crystal.

DETAILED DESCRIPTION

Figure 4:
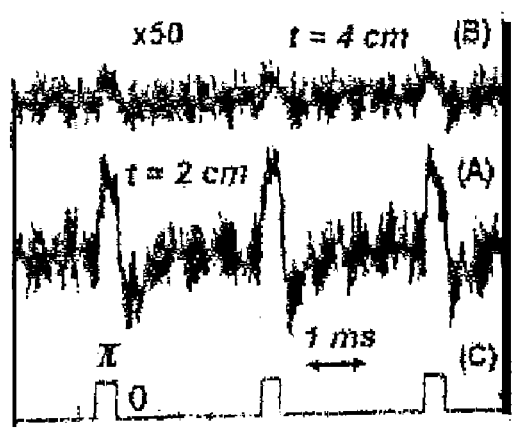
FIG. 4 represents a signal obtained on an oscilloscope screen for two objects to be imaged.

FIG. 1 diagrammatically represents an acousto-optic imaging installation that can be used in the context of the invention.

There is an object 1 to be imaged using said installation. This object is a scattering medium, typically of a thickness e of a few centimeters and can, for example, be a biological tissue, such as a part of the human or animal body, or other.

A piezo-electric transducer 2 is in acoustic contact with the object 1, either directly in contact or, for example, acoustically coupled to the object 1 by the immersion of the latter in a tank 3 filled with water 4. For example, a Panametrics piezo-electric transducer of diameter 37 mm with a spherical output face of radius 75 mm is used. The transducer vibrates the area of the object that is in line with it, and in particular the area 5 at the ultrasound acoustic frequency $f_a$, such as for example 2 MHz. The piezo-electric transducer 2 is placed facing a given position of the surface of the object. The piezo-electric transducer 2 is also designed to focus on a given area 5 of the object to be imaged for which optical information is required.

There are also control means (not shown), of microcomputer or other type, designed to change the focal length of the piezo-electric transducer 2 and to control the displacement of the latter facing the surface of the object 1 to be imaged, so as to scan the object 1 to be imaged in one, two or three dimensions.

There is also a light wave generation device GEN designed to generate two coherent light waves, frequency-shifted by approximately the value of the acoustic frequency $f_a$ imparted by the piezo-electric transducer 2 to the area 5 of the object 1 to be imaged. Other types of devices than the one described below can also be used for this purpose.

There is a laser 6, which is, for example, a single-frequency YAG laser with a wavelength of 1.06 μm and a power of 100 mW. The laser 6 emits an initial optical wave INI exhibiting, in the example under consideration, a vertical polarization. The initial wave INI is split into a first beam F1 and a second beam F2 by a splitting prism 7, for example a 50% splitting prism whereby the power available on each beam F1, F2 is approximately 50 mW.

Use is also made of a first acousto-optic modulator 8a and a second acousto-optic modulator 8b, respectively receiving the beams F1 and F2 as input. These acousto-optic modulators 8a and 8b are, for example, modulators from the company Cristal Technology, comprising an acousto-optic cell of tellurium dioxide (TeO$_2$) driven by a sinusoidal radio-frequency clock of frequency df, transmitting, from the wave that is applied to it, both a non-diffracted beam and a diffracted beam frequency-shifted by the value df relative to the wave that is applied to it. As an example, the first acousto-optic modulator 8a is driven by a clock of frequency df=73 MHz and delivers as output a wave that will hereinafter be called the incident wave INC frequency-shifted by 73 MHz relative to the initial wave INI. The second acousto-optic modulator 8b is of similar design and is driven to a frequency of 75 MHz and delivers as output a wave that will hereinafter be called pump wave PMP frequency-shifted by 75 MHz relative to the initial wave INI. By using acousto-optic modulators 8a, 8b with an efficiency of approximately 50%, a power of approximately 25 mW is thus available for each of the incident INC and pump PMP waves in the concerned example.

There are thus generated two mutually-coherent light waves, frequency-shifted by a value approximately equal to the acoustic frequency applied by the piezo-electric transducer 2 to the object 1 to be imaged.

Figure 5A:
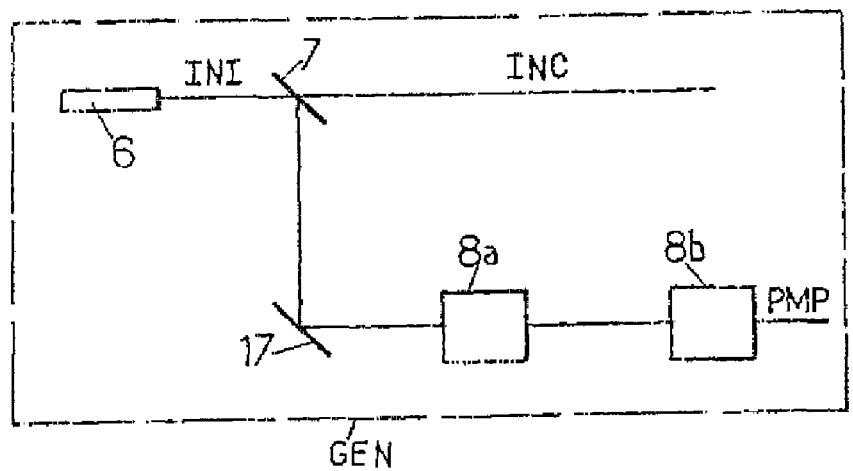
FIGS. 5a and 5b are diagrammatic views of two variants of embodiment of a light wave generation device.

According to a first variant of the light wave generation device GEN, represented in FIG. 5a, the incident wave INC passes through no acousto-optic modulator, while the pump wave is frequency-shifted, relative to the incident wave, by a first frequency $df_1$=−73 MHz by the first acousto-optic modulator 8a, then shifted by a second frequency $df_2$=+75 MHz by the second acousto-optic 8b, such that $df_1+df_2 \cong fa$.

Figure 5B:
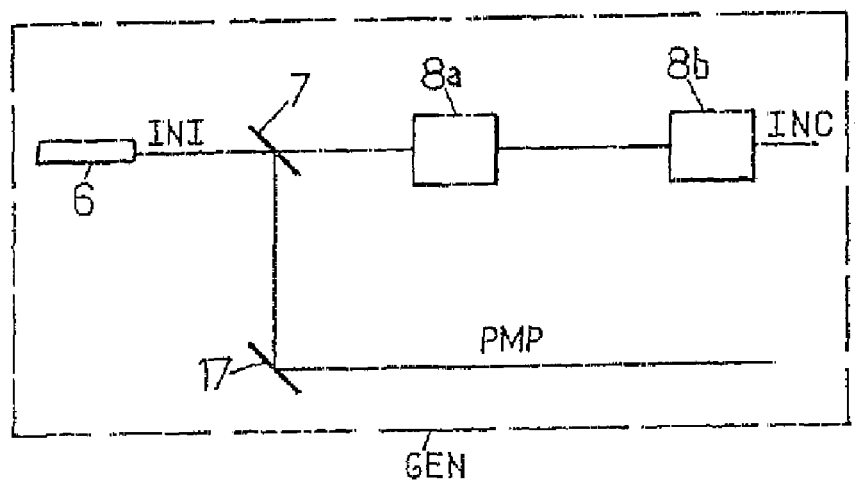

According to a second variant of the light wave generation device GEN, represented in FIG. 5b, the incident wave INC is frequency-shifted, relative to the initial wave, by a first frequency $df_1$=+73 MHz by the first acousto-optic modulator 8a, then by a second frequency $df_2$=−75 MHz by the second acoustic modulator 8b, and the pump wave PMP is not frequency-shifted relative to the initial wave INI, such that $f_{INI}+df_1+df_2+f_a \cong f_{PMP}$, where $f_{INI}$ is the frequency of the initial wave and $f_{PMP}$ the frequency of the pump wave.

Thus, according to the variants of FIGS. 1, 5a and 5b of embodiment of a generation device GEN, a first shift device, inserted between the laser 6 and the object 1 to be imaged, comprises one, zero or two acousto-optic modulators, and a second shift device, inserted between the laser 6 and the holographic material 9, respectively comprises one, two or zero acousto-optic modulators. Thus, a "shift device", in the sense of the present description can, if necessary, comprise no element.

The rest of the description is given for the exemplary embodiment of the generation device of FIG. 1.

The incident wave INC obtained from the first acousto-optic modulator 8a is applied to the object 1 to be imaged at any point, not necessarily linked to the position in the object 1 to be imaged of the area 5. The light is scattered by the object 1 and generates a signal wave SIG extending in a wide solid angle behind the imaged object 1 relative to the direction of application of the incident wave INC. Some photons of the incident wave are scattered by the object 1 to be imaged without passing through the vibrating area whereas other photons passing through the vibrating area are subject to the acousto-optic effect. Consequently, the signal wave SIG mainly comprises two components: on the one hand, the "carrier" component, at the frequency $f_I$ of the incident wave INC, which corresponds to the photons not passing through the vibrating area, and on the other hand, an acousto-optic component of frequency $f_{AO}=f_I \pm f_a$ corresponding to the photons passing through the area 5 of the object 1 to be imaged. It is this acousto-optic component that carries the information relating to the area 5 of the object 1 to be imaged that is being measured.

To this end, and according to the invention, there is available a dynamic holographic material 9 such as a photo-refractive crystal, for example made of gallium arsenide (AsGa), measuring 1 cm×1 cm×1 cm. Such photo-refractive crystals, for example described in U.S. Pat. No. 5,131,748, are holographic materials in which the interference of a signal wave and of a pump wave forms a refraction index grating. This refraction index grating can have a static component according to the characteristics of the pump and signal waves, and such a static refraction index grating diffracts the pump wave applied to the photo-refractive crystal to form a diffracted wave DIF. For the photo-refractive crystal 9, it would also be possible to use a material of the sillenite type such as BSO, BGO or STO, an iron-doped indium phosphide (InP), a vanadium-doped cadmium telluride (CdTe), a tin hypothiodiphosphate crystal (SPS), or any other suitable material.

Instead of the photo-refractive crystal, it would also be possible to use an inverted laser medium such as YAG or titanium-sapphire as the dynamic holographic material. In such a material, subject to the pumping by an appropriate laser, a population inversion occurs making it possible to form therein a complex index grating in the form of a gain grating. These materials are particularly advantageous because they are sensitive to wavelengths between 770 nm and 1 μm, which are wavelengths that are useful in biology.

In the described example, the signal wave SIG is applied to a first side $9a$ of the photo-refractive crystal 9. For example, using a first optical device formed by two wide-aperture lenses 10, 11, an image of the "rear" side $1a$ of the object 1 to be imaged is formed on the side $9a$ of the photo-refractive crystal 9. The lenses 10 and 11 are positioned so as to recover the greatest possible proportion of the SIG wave, scattered in a wide solid angle, on the side $9a$ of the photo-refractive crystal.

The pump wave PMP generated by the generator device GEN (for example, the wave obtained from the second acousto-optic modulator $8b$) is applied to the photo-refractive crystal 9, for example, to a side $9b$ of the crystal orthogonal to the side $9a$ using a second optical device such as a reflecting plate 16.

The interference between the signal wave SIG and the pump wave PMP produces a volumic interferogram inside the photo-refractive crystal 9. This interferogram comprises, on the one hand, a component linked to the carrier component of the signal wave and, on the other hand, a component linked to the acousto-optic component of the signal wave. For a frequency shift between the incident wave INC and the pump wave PMP equal to the frequency $f_a$ of the acoustic wave, the component of the interferogram associated with the acousto-optic component of the signal wave SIG (of frequency $f_l \pm f_a$) is static since the frequency of the pump wave PMP is equal to the frequency of this acousto-optic component of the signal wave. However, the component of the interferogram formed between the incident wave and the pump wave gives a temporal modulation at the acoustic frequency. This variation is too rapid for an index grating to be inscribed in the dynamic holographic medium. Thus, by photo-refractive effect, the static interferogram associated with the acousto-optic component creates, in the crystal, an index grating that reproduces the speckle figure associated with said acousto-optic component which is generated by the vibration of the sample at the acoustic frequency $f_a$, mainly in the area 5, and which therefore characterizes the optical properties of the sample in this area.

Simultaneously or subsequently, the pump wave applied to the photo-refractive crystal 9 is diffracted by the index grating formed in the crystal, in the same direction as the signal wave SIG. Since the index grating registers the spatial structure of the acousto-optic component of the signal wave SIG, the wave DIF diffracted by the crystal has the same spatial structure as the latter. The interference between the signal wave SIG and the diffracted wave DIF therefore remains spatially coherent with itself over the entire surface of the crystal 9. It is thus possible to observe this interference with a single-pixel detector 12, such as a silicon photodiode. It is possible to use a third optical device formed by the wide-aperture lenses 13, 14 to form an image of the side $9c$ on a remote photodiode 12. If the photodiode is much smaller than the surface area of the side $9c$ of the crystal 9, a lens 15 can be used that concentrates the light on the photodiode 12.

Applying the signal wave and the pump wave to two orthogonal sides of the dynamic holographic material limits the influence, on the detected signal, of the assembly imperfections of the installation and of the crystal, which are not scattered towards the detector, but in the direction of the pump wave.

It is also possible to choose to increase the speed with which the photo-refractive effect is set up in the crystal by reducing the angle between the signal wave and the pump wave, while keeping a non-zero angle. It is thus possible to apply both waves to the same side of the crystal. However, the influence of the assembly imperfections and the imperfections of the crystal will be more sensitive on the detector. It is also possible to choose an intermediate angle providing a good trade-off between these two options.

The light intensity thus detected on the photodiode 12 makes it possible to obtain information concerning the area 5 of the object 1 to be imaged, and by moving the focal length of the piezo-electric transducer 2, or the transducer itself to the surface of the object 1, it is possible to form a one-, two- or three-dimensional image of the object. This image can also be coupled to an image by ultrasound (echography) simultaneously formed of the object 1, because the used piezo-electric transducer 2 used can be of the type of those to generate such an ultrasound image.

In the context of the invention, it is also possible to improve the detection quality on the detector 12, as described below.

The use of a photo-refractive crystal 9 makes it possible to eliminate the noise due to the unmarked component of the signal wave because the photo-refractive effect that takes place in the crystal is selective, and occurs only for the acousto-optic component of the signal wave SIG. Indeed, the pump wave PMP is at the same frequency as the acousto-optic component. In these conditions, only the interference between the pump wave PMP and the acousto-optic component of the signal wave SIG remains stable over time, and is therefore capable of generating an index grating in the crystal 9. This static interference signal is difficult to distinguish from the continuous background noise due, for example, to the dark current of the photodiode, the impurities of the photo-refractive crystal, or other causes. To make the interference visible against this continuous background noise, it is preferable to have an interferogram varying in time which leads to a temporal modulation of the signal obtained on the photodiode 12. To this end, one of the waves involved in generating the interferogram can be amplitude- or phase-modulated.

For example, it is possible to phase-modulate the incident wave INC on the object 1 to be imaged, the pump wave PMP generated on the side $9b$ of the photo-refractive crystal 9, or the acoustic wave generated by the piezo-electric transducer 2. These three options are all possible, and there follows, by way of example, a description of the phase-modulation of the acoustic wave.

To obtain a temporal modulation of the signal on the photodiode, the modulation of the acoustic wave needs to satisfy the following three conditions:
  the modulation must be faster than the time needed to form the index grating in the photo-refractive crystal 9 (in order for the index grating, which performs an averaging, not to be affected by the modulation),
  the modulation must be of good amplitude (which allows for a good detection sensitivity), and
  the modulated wave must not exhibit, during the time needed to form the index grating, a zero average value (in order for the index grating, which depends on the average value of the signal wave SIG, to be able to exist).

Numerous modulations can satisfy these conditions. As an example, FIG. 2 shows a modulation satisfying these criteria. The acoustic phase φ is modulated into rectangular pulses of φ=0 to φ=π. The duty cycle of the rectangular pulses is taken to be different from ½, and is, for example, taken to be equal to ⅛ for a pulse frequency of 302 Hz.

The acousto-optic component of the signal wave SIG is linked to the acoustic wave applied by the transducer 2. Consequently, the phase of the acousto-optic component of the signal wave exhibits the same phase modulation as the acoustic wave. The acousto-optic component of the signal wave then exhibits a non-zero average value equal to ⅝ of the value of the acousto-optic component of the signal wave on a phase shift φ=0. The index grating formed in the photo-refractive crystal 9 is non-zero, and corresponds to the average value $<E_{AO}>$ of the acousto-optic component of the signal wave SIG.

In the example under consideration, the photo-refractive crystal 9 has sides 9a, 9b, 9c oriented so that the crystal 9 exhibits a so-called "energy transfer" configuration. In this configuration, the diffracted wave DIF has the same polarization as the acousto-optic component of the signal wave. Furthermore, the diffracted wave DIF is in phase with $<E_{AO}>$, that is, in phase with $E_{AO}$ (φ=0).

The phase modulation φ of the acoustic wave is reflected in a modulation of the signal $|E|^2$ seen by the photodiode 12, which is illustrated in FIGS. 3a and 3b.

In FIG. 3a, when the phase modulation φ is equal to 0 ("writing" step), the diffracted wave DIF is in phase with the acousto-optic component of the signal wave. The amplitude E in the crystal 9 is maximum and corresponds to the sum of the amplitudes $E_{dif}$ and $E_{AO}$ respectively of the diffracted wave and of the acousto-optic component of the signal wave. The signal seen by the photodiode, which is proportional to the intensity $I=\int E f^2$, is also maximal.

In FIG. 3b, when the phase modulation φ is equal to π ("reading" step), the diffracted wave DIF is in phase opposition with the acousto-optic component of the signal wave. The total amplitude E, now corresponding to the subtraction of the amplitude of the acousto-optic component of the signal wave $E_{AO}$ and the amplitude of the diffracted wave $E_{dif}$, is minimal as is the signal seen by the photodiode.

FIG. 4 shows an oscilloscope screen on which the signal (C) represents the phase modulation of the acoustic wave applied to the object to be imaged, exhibiting a duty cycle of ⅛ and a frequency of 305 Hz, the signal (A) represents the signal detected for an object to be imaged which is a 2 cm thick piece of chicken fillet, and the signal (B) represents the averaged detected signal, enlarged 50 times, fox a 4 cm thick piece of chicken fillet.

For other configurations, such as, for example, in the case of a pumped laser medium, the roles can be reversed. There is then phase opposition for φ=0 and signals in phase for φ=π.

The information relating to the area 5 of the object 1 to be imaged can be extracted by synchronous detection of the signal detected by the photodiode 12.

The photo-refractive crystal 9 is not necessarily used in an "energy transfer" configuration. It could also be used in an "anisotropic" configuration, by using a crystal having differently oriented sides 9a, 9b. The acousto-optic component of the signal wave and the wave diffracted by the index grating then have orthogonal polarizations To make the two waves interfere, it is possible, for example, to use a quarter-wave plate and a polarizing cube, in a manner that is known. An example of phase modulation that can be used in this configuration is to use a pulsed phase modulation from 0 to π/2 with a duty cycle of 50%. A linear detection can thus be obtained.

The installation described here makes it possible to obtain good-quality images, particularly because it allows for detection over a wide optical expanse with a photodiode, which was not the case with the devices of the prior art.

The frequency selectivity of the photo-refractive effect is characterized by the time $T_p$ needed to form the index grating, and by the frequency difference $f_a$=2 MHz between the carrier component of the signal wave and the pump wave PMP. The photons associated with the component of the signal wave do not create index grating when $T_p \times f_a \gg 1$.

This selectivity condition is very widely implemented. In the example described here, we have, for example, $T_p$=1 to 10 ms, which corresponds to $T_p \times f_a = 10^3$ to $10^4$.

Such an installation makes it possible to increase the measurement speed compared to the installations known from the prior art. Increasing the measurement speed means reducing the measurement time, and therefore the forming time $T_p$. This forming time can easily be reduced by increasing the power of the pump wave PMP compared to the proposed example. For example, by increasing the power of the initial wave INI, both the power of the incident wave INC and the power of the pump wave PMP are increased. On the one hand, an increase in the power of the pump wave PMP reduces the forming time. On the other hand, an increase in the power of the incident wave INC increases the signal. Compared to the proposed example, it is possible in particular to increase the power of the initial wave, and therefore the power of the incident wave, while remaining within the safety limits imposed for dealing with human tissues, the power of the pump wave poses no safety problems, since the pump wave does not pass through the sample.

Compared to the described example, it is possible, with embodiment variants, to implement one and/or another of the following arrangements:
   use a more powerful laser,
   use wider-aperture lenses 10, 11, 13, 14 so as to retain the same angular aperture with a greater diode area,
   use a lower-noise photodiode 12, such as a Peltier-cooled photodiode,
   use a photodiode with a larger area.

All these arrangements would make it possible to increase the signal/noise ratio of the detection.

The invention claimed is:

1. An acousto-optic tomographic imaging method for an object comprising steps during which:
   (a) the vibration of a three-dimensional area of the object is generated by applying an acoustic wave exhibiting a certain acoustic frequency to the object,
   (b) an incident wave and a pump wave are generated by:
      generating an initial light wave with a light wave generating device, and
      splitting said initial wave into a first beam and a second beam;
      shifting the frequency of said first beam by a first frequency shift in order to generate the incident wave,
      shifting the frequency of said second beam by a second frequency shift in order to generate the pump wave, said second frequency shift being roughly equal to the sum of the first frequency shift and the acoustic frequency;
   (c) an incident light wave is applied to said object and a signal light wave is generated by travelling through the object and interacting with the three-dimensional area of the object, said signal light wave comprising at least one acousto-optic component frequency-shifted by said acoustic wave,
   (d) a light pump wave is generated, coherent with said incident wave at a frequency similar to the frequency of said acousto-optic component, (e) a complex index grating is formed in a dynamic holographic material by applying said signal wave and said pump wave to said material, and (f) a digital parameter relating to the light intensity in this three-dimensional area is obtained from said complex index grating.

2. The method as claimed in claim 1, wherein, during the step (f), (f1) a diffracted wave is generated by applying said pump wave to said complex index grating, and (f2) the interference between said diffracted wave and said signal wave is detected using a photodetector.

3. The method as claimed in claim 1, wherein a phase modulation is applied to a wave chosen from the acoustic wave, the pump wave, and the incident wave.

4. The method as claimed in claim 3, wherein said phase modulation is applied to the acoustic wave.

5. The method as claimed in claim 1, wherein an amplitude modulation is applied to a wave chosen from the acoustic wave, the pump wave, and the incident wave.

6. The method as claimed in claim 5, wherein said amplitude modulation is applied to the acoustic wave.

7. The method as claimed in claim 1, wherein the light wave generating device is a laser.

8. The method as claimed in claim 1, wherein one of said first and second frequency shifts is zero.

9. The method as claimed in claim 1, wherein, during the step (d), said signal wave is applied to a first side of said dynamic holographic material and said pump wave is applied to a second side of said material, different from the first side.

10. The method as claimed in claim 1, wherein, during the step (d), said signal wave and said pump wave are applied to one and the same side of the dynamic holographic material.

11. The method as claimed in claim 1, wherein said dynamic holographic material is a photo-refractive crystal adapted to operate in "energy transfer" mode.

12. The method as claimed in claim 1, wherein said dynamic holographic material is a photo-refractive crystal adapted to operate in "anisotropic diffraction" mode.

13. The method as claimed in claim 1, during which digital information is also obtained relating to a second area of the object by applying the following steps:

(a') the vibration of said second area is generated by applying an acoustic wave at an acoustic frequency to the object at said second area, and the steps (c) to (f) are repeated for said second area.

14. An acousto-optic imaging installation for an object comprising:

(A) a transducer designed to generate the vibration of an area of the object by applying an acoustic wave having an acoustic frequency to the object, (B) a device for generating light waves designed to apply to said object an incident light wave and thus generating a signal light wave comprising at least one acousto-optic component frequency-shifted by said acoustic wave, and also designed to generate a light pump wave, coherent with said incident wave at a frequency similar to the frequency of said acousto-optic component, (C) a dynamic holographic material adapted so that a complex index grating is formed by the application to said material of said signal wave and of said pump wave, and (D) a detection device designed to obtain a digital parameter relating to the light intensity in this area from said complex index grating.

15. The installation as claimed in claim 14, wherein said detection device comprises a detector designed to detect the interference between a diffracted wave generated by said pump wave passing through said complex index grating, and said signal wave.

16. The installation as claimed in claim 15, wherein said detector is a single-pixel photodiode.

17. The installation as claimed in claim 15, comprising:

a first optical device designed to apply the signal wave to a first side of the dynamic holographic material, a second optical device designed to apply the pump wave to a second side of the photo-refractive material, and a third optical device designed to form on said detector an image of a third side of the dynamic holographic material opposite to said first side.

18. The installation as claimed in claim 17, wherein said first and second sides of dynamic holographic material are the same.

19. The installation as claimed in claim 17, wherein said second side of dynamic holographic material is orthogonal to said first side.

20. The installation as claimed in claim 14, wherein the generation device comprises:

a laser designed to emit an initial light wave, a splitter device designed to generate from said initial wave a first beam and a second beam, a first shift device designed to shift said first beam frequency-wise to generate said incident wave, and a second shift device designed to shift said second beam frequency-wise to generate said pump wave, said first and second shift devices being designed for said pump wave to exhibit a frequency roughly equal to the sum of the frequency of the incident wave and the frequency of the acoustic wave.

21. The installation as claimed in claim 20, wherein said first shift device comprises one or two acousto-optic modulators, and wherein said second shift device comprises, respectively, one or two acousto-optic modulators.

22. The installation as claimed in claim 14, wherein said dynamic holographic material is a photo-refractive crystal.

23. The installation as claimed in claim 14, wherein said dynamic holographic material is a population inversion material designed to be formed with a complex index grating in the form of a gain grating, said installation also comprising an energy source designed to maintain said population inversion in said material.

24. The installation as claimed in claim 14, also comprising a control device designed to cause said transducer to be displaced.

25. The installation as claimed in claim 14, also comprising a control device designed to cause the focal length of said transducer to be changed.

26. The installation as claimed in claim 20, wherein said first shift device comprises zero acousto-optic modulator, and wherein said second shift device comprises two acousto-optic modulators.

27. The installation as claimed in claim 20, wherein said first shift device comprises two acousto-optic modulators, and wherein said second shift device comprises zero acousto-optic modulator.

* * * * *